United States Patent [19]

Fulkerson

[11] 4,099,406
[45] Jul. 11, 1978

[54] DEVICE FOR AUTOMATICALLY TESTING FLUID ABSORPTION RATES OF SOIL

[75] Inventor: Melvin A. Fulkerson, Burnsville, Minn.

[73] Assignee: Hammer Industries Inc., Minneapolis, Minn.

[21] Appl. No.: 774,922

[22] Filed: Mar. 7, 1977

Related U.S. Application Data

[63] Continuation-in-part of Ser. No. 630,405, Nov. 10, 1975, abandoned.

[51] Int. Cl.² ............................................. G01N 5/02
[52] U.S. Cl. ...................................... 73/73; 73/304 R
[58] Field of Search ........... 73/304 R, 73, 223, 304 C, 73/155, 113, 114, 38

[56] References Cited

U.S. PATENT DOCUMENTS

| 2,540,096 | 2/1951 | Bull .................................... 73/38 |
| 3,368,404 | 2/1968 | King ................................ 73/304 R |
| 3,930,411 | 1/1976 | Beeker et al. ...................... 73/304 C |

*Primary Examiner*—Donald O. Woodiel
*Attorney, Agent, or Firm*—James R. Cwayna

[57] ABSTRACT

A device for the automatic determination and recordation of rates of fluid absorption in soils, including a plurality of conductive probes which are positioned at various levels with regard to a provided water level such that as the water level drops, the time to accomplish the drop is recorded. The device provides a pair of timing and time recording devices interconnected with the probes such that two individual time sequences may be recorded.

13 Claims, 4 Drawing Figures

DEVICE FOR AUTOMATICALLY TESTING FLUID ABSORPTION RATES OF SOIL

BACKGROUND AND OBJECTS OF THE INVENTION

This application is a continuation-in-part application of an application filed Nov. 10, 1975, Ser. No. 630,405 entitled Device for Automatically Testing Fluid Absorption Rates of Soil, now abandoned.

FIELD OF THE INVENTION

This invention relates generally to what are known in the art as percolation devices and more particularly to a percolation tester which provides means for automatically determining the time necessary for the water to be absorbed in the ground or other medium being tested.

The use of percolation tests in soil testing, such as to determine proper sewage disposal systems is well known in the art. Basically, the testing requires a time determination for the water to be absorbed into the soil at a specific location. This is normally accomplished by providing a test hole, filling the hole with a quantity of water, floating an indicator on the fluid surface and timing the period for the indicator to drop a certain distance, or conversely, recording the various distances dropped with respect to a fixed time period. This timing may take a relatively long period and the cost of performing such a simple percolation test may be relatively expensive.

This simple process has been made more difficult by certain health standards that require that the water remain in the test hole for a predetermined period before the actual percolation test is performed. This time is termed a saturation time or soak time and a percolation test performed prior to a standard for saturation is, in many cases, held to be invalid. Obviously, if personnel is required to continually monitor this dual test situation, the cost of testing becomes extremely high.

With applicant's device, means are provided to time and record both of these required times and through such a device, it is not necessary that the tests be continually monitored. Applicant's unit provides the means and apparatus for timing the required operations and for recording the results therefrom for subsequent retrieval and reviewal which means will only require personnel for the initial installation of the unit and ultimate removal and reading of the recording devices of the unit.

It is therefore an object of applicant's invention to provide a device for the automatic testing of fluid absorption rates of soils.

It is a further object of applicant's invention to provide a device to determine the time of soil exposure to fluid prior to the performance of a percolation test of the soil.

It is a further object of applicant's invention to provide a testing device which is capable of timing a first fluid to soil exposure situation, recording the smae and thereafter timing the drop of the fluid level over a particular distance and recording this time.

It is still a further object of applicant's invention to provide a device capable of being adjusted for selected, predetermined water level drops and timing the period for the water level drop.

These and other objects and advantages of applicant's invention will more fully appear from a consideration of the following specification set forth in connection with the accompanying drawings in which the same numeral is used to designate the same or similar parts throughout the several views, and in which.

Figure 1:
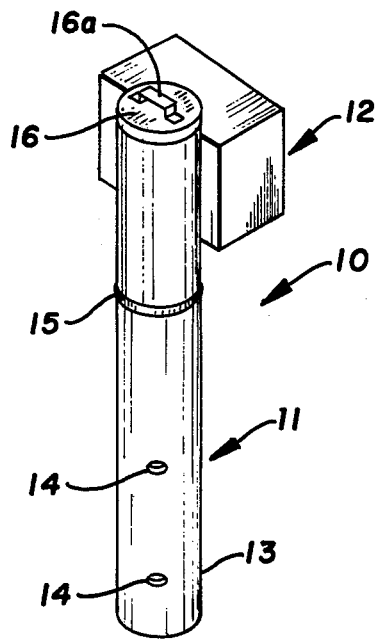
FIG. 1 is a perspective view of a percolation tester arranged and constructed in accordance with the applicant's invention.
Figure 3:
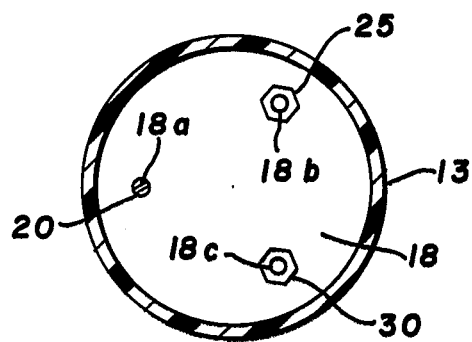
FIG. 3 is a horizontal section taken substantially along Line 3—3 of FIG. 2; and, FIG. 4 is a schematic illustration of a control, timing and readout circuit.
Figure 2:
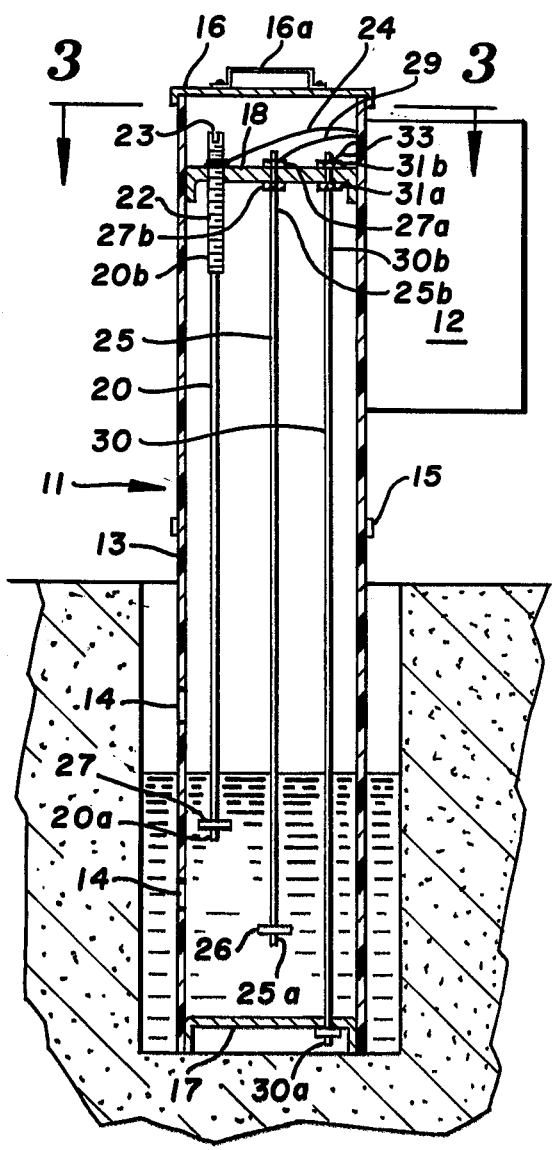
FIG. 2 is a vertical section taken substantially centrally through the percolation tester as illustrated in FIG. 1.

In accordance with the accompanying drawings, applicant's percolation device is generally designated 10 and basically consists of a probe housing or test insertion portion 11 and a control, timing and readout portion 12. As will become obvious through a reading of this specification, the housing portion 11 is designed to be inserted into a test hole while maintaining the control and readout portion 12 in elevated position above ground level. To provide for this situation, the housing 11 provides a longitudinally extending open top and open bottom, hollow member 13 having a plurality of apertures 14 formed adjacent the lower end thereof and extending therethrough to permit a free flow of the fluid within the hole therethrough. The housing 11 provides a protective arrangement for the probes that are positioned therein. The housing 13 is of a non-conductive material for reasons that will become obvious hereinafter. The apertures 14 are arranged adjacent to an may be spaced longitudinally along the lower portion of the hollow member 13, as this portion of such unit, in practice will be the only portion of the unit that will be exposed to water.

Marking indicia 15 is provided about the outer periphery of the hollow member 13. This indicia is only to insure to the user that the unit has been properly positioned within the test hole. The portion of the housing below the marking 15 should be inserted into the test hole, with the remainder of the unit being positioned above ground level.

A first anchoring member 17 is provided adjacent the lowermost end of the housing 11 and this member17 is, in the form shown, of a U-shaped configuration, to permit the same to be easily attached to the inner surface of the hollow element 13. In the form shown, this member, 17, is of a non-conductive material and is of a minimal cross-section to allow for free water circulation therepast. It should be obvious that this anchoring member could consist of an inwardly directed tab secured to the inner wall of the hollow element 13.

A second anchoring and positioning element 18 is secured to the upper portion of the hollow element 13 and this element, 18, in the form shown, is arranged to fit into the interior of the hollow element 13 such that the individual porbes 20, 25 and 30 may be positioned and spaced thereon to prevent contact therebetween. This second anchoring element 18 is also of a non-conductive material to electrically isolte the probes 20, 25 and 30.

A cover member 16 is arranged to close the upper end of the hollow element 13 and a handle member 16a may be positioned thereon to assist in removal and in handling of the unit.

Obviously, since the unit is arranged to test a drop in water levels, and water is a conductor of electricity, it is essential that the unit be arranged and constructed to be responsive to the water levels being monitored and eliminate any outside water which would serve as a conductor.

First probe 20, consists of a longitudinally extending, electrically conductive member having an upper and a lower end. The lower end of probe 20, designated 20a, is provided with a non-conductive, radially extending, spacer element 21 to prevent the probe 20 from physically contacting the other probes of the unit and to prevent contact of the same with the housing inner surface. The upper end 20b of the probe 20 is provided with, in the form shown, a threaded section 22, which section is received into a threaded aperture 18a in the second anchoring element 18. A slot 23 may be provided in the uppermost end of the probe 20 such that the same may be rotated to control the position of the bottom end 20a thereof.

A conductor 24 is provided from the upper end 20b of the probe 20 and extends therefrom to the control, readout and timing portion 12 of the unit.

The threaded upper end and the threaded aperture 18a for the adjustment of probe 20 should not be considered to be a limiting factor of the invention. The concept of such adjustability may be achieved through various means. As shown, the second anchoring and positioning element 18 is located at the upper end of the hollow element 13 and depending upon the adjustment required for probe 20, it may be necessary to cut the upper end of the same such that the probe will not interfere with the closing of the cover 16. Applicant has provided a means for cutting the upper end of the probe 20 and this includes notching the upper end of the probe and this notching may be randomly spaced or incrementally spaced, which incremental spacing would assist the user in determining the extension of the probe 20 into the housing and its relation to the other probes and particularly probe 25.

The necessity for such probe adjustment is the various requirements established by the individual State bodies. Certain States will require a percolation test based on, for example, a one inch drop, while others will require a two or more inch drop. Applicant's adjustments take these conditions into consideration.

Probe 25 comprises a longitudinally extending, electrically conductive member, having a radially extending spacer element 26 adjacent the lower end 25a thereof, with the upper end 25b thereof arranged to pass through and aperture 18b in the second anchoring element 18. Anchoring means 27a, 27b may be provided on each side of the anchoring element 18 to position the probe 25 with respect thereto. A conductor 29 is connected to probe 25 and extends therefrom to the control section 12.

The third probe 30, is a stationery probe and is secured to both the first and second anchoring elements 17, 18. The lower end 30a of probe 30 is arranged and constructed to pass through and be otherwise anchored to the first anchoring element 17 and the upper end thereof 30b is arranged to be connected to the second anchoring element 18, as for example, by passing through aperture 18c thereof and being secured thereto with connective members 31a, 31b. A conductor 33 is attached to the upper end 30b of probe 30 and extends to the control portion 12.

As will be explained hereinafter, the stationary probe 30 provides the circuit continuity for each of the other probes 20, 25 with the water in the test hole providing a conductive medium therebetween.

Figure 4:
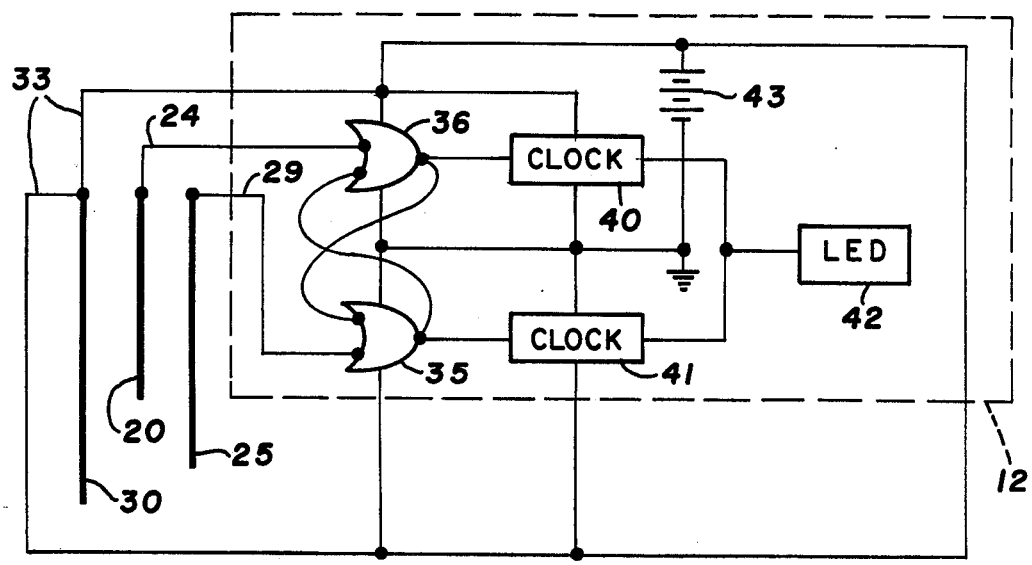

The operation of the unit for the timing of the various functions of the device, the storage of the information related to the timing and the ultimate retrieval of this information is illustrated in FIG. 4.

The operation of this unit provides a means for determining what may be and is known in the art as a saturation time and also provides a means for determining what may be and is known in the art as a percolation time. Many testing situations require that the soil reach a saturated condition before the percolation test is accepted as being valid. To determine the saturation of the soil it has been established that the soil be exposed to water for a predetermined amount of time prior to the percolation test. Applicant's device provides the means for determining whether or not such a predetermined time has been met and to thereafter provide the timing for the percolation test.

To provide for these two distinct features, applicant provides a first saturation timing arrangement and a second percolation timing arrangement with the ability to record and read the results thereof independently.

As illustrated in FIG. 4, the circuitry includes the probes 20, 25 and 30, a pair of switching or gate members 35, 36, a pair of timing or clock mechanisms 40, 41; a source of power for the circuit 43 and an operative indicator 42. With the exception of the probes 20, 25 and 30, the remaining portion of the circuti is indicated as being encompassed within the control section 12 of the unit. The aforementioned conductors 24, 29, 33 are arranged to conduct from the probes 20, 25 and 30 into control section 12.

The switching mechanisms, 35, 36, in the form shown, are defined as 1 piece CMOS devices and are 14 Pin DIP (Dual In-Line Package Units) and are commonly known in the art as NAND Gates and find their comparative structure as electrical relays. Such devices are commercially available and one source of such devices is Radio Corporation of America and the part number therefore is CD4001AE. Other manufacturers of such Flip-Flop Transistorized units are available and the operation of such units is identical to the device employed herein.

The timing or clock mechanisms are simple timing devices and applicant has found that such a device manufactured and made available by Seth Thomas is suitable for this circuitry. This particular device is known as an Isotron No. 101 which is basically a battery powered wall clock.

The operative indicator 42 is commonly known as an LED, Light Emitting Diode, and the function of this device is simply to indicator the operation of either of the timing clocks 40, 41.

Applicant's choice of NAND Gates will provide a particular mode of operation but this should not be considered to be limiting to the concept of the application for if the opposite of such a NAND Gate, an AND Gate is utilized the final operation of the device will be exactly the same. The operation of these units is to provide a switching and control function in response to the level of the water within the test hole and either mode or element chosen will give the same function.

As previously explained in the specification, water is introduced to the unit after the same has been inserted into the test hole and at this time the two probes 20 and 25 will be in conducting relation through the circuitry established by the water level and the probe 30, water being above the lower level of probe 20, and a signal is provided to both switching mechanisms 35, 36 which will provide a signal to clock 40 and will also provide a signal to the operative indicator 42. When the water level drops below the lower end of probe 20, probe 20 will be removed from the circuitry and the result will be that clock 40 will be deenergized and clock 41 will be energized and the operative indicator will also be energized. When the water level drops below the level of probe 25, clock 41 will be deenergized as will be the operative indicator 42.

The clocks may be considered to be recording or storage devices as upon deenergization thereof, they will retain the stopping time and the operator will be able to ascertain the time of both the saturation, which would be provided on the clock 40 and the percolation time as provided on clock 41. The operator is also informed as to the finish of testing or timing due to the indicator 42.

With applicant's device, a single mode of operation has been discussed but it should be obvious that this same switching circuitry and timing arrangement may be altered such that clock 40 operates only during the saturation timing and that clock 41 is energized only after clock 40 is deenergized or that both clocks will operate during the saturation timing and that clock 41 will continue to operate thereafter and after the deenergization of clock 40. The variations of such operation will only present a substraction problem to the user of the device, but will not hamper the results obtained from the unit.

With applicant's device it is possible to time both the saturation time and the percolation time for proposed sewage arrangements without requiring constant supervision and from the information received and made available in such tests by such equipment, the builder or land user will be able to conform to the required building codes.

Applicant has provided herein a unique device for the timing of water level drops without requiring constant maintenance and which permits a degree of adjustability to conform the unit to applicable codes.

What I claim is:

1. A device for timing fluid absorption into soils to establish a rate of absorption, said device including:
   a. a first, electrically conductive, longitudinally extending probe, of a first predetermined length and having a first and a second end;
   b. a second, electrically conductive, longitudinally extending probe, of a second predetermined length shorter than that of said first probe and having a first and a second end;
   c. a third, electrically conductive, longitudinally extending probe, of a third predetermined length shorter than that of said second probe and having a first and a second end;
   d. means for mounting said first ends of said probes in generally planar relation such that said second ends of said probes will be displaced unequally from said mounting means;
   e. means supporting said mounting means with respect to the soil to be tested such that said probes may extending downwardly into a test hole into the soil to be tested;
   f. a first timing means connected to said first and third probes and controlled by the conductivity therebetween for actuation of said first timing means in response to conduction between said probes provided by fluid within the test hole; and,
   g. a second timing means connected to said first and second probes and controlled by the conductivity therebetween for actuation of said second timing means in response to conduction between said probes provided by fluid within the test hole.

2. The structure set forth in claim 1 and switching means deactivating said first timing means upon a loss of conductivity between said first and third probes.

3. The structure set forth in claim 2 and switching means activating said second timing means upon a loss of conductivity between said first and third probes.

4. The structure set forth in claim 3 and said switching means deactivating said second timing means upon a loss of conductivity between said first and second probes.

5. The structure set forth in claim 1 and said first timing means connected to an operative indicator device for indication of the operative mode thereof.

6. The structure set forth in claim 1 and said second timing means connected to an operative indicator device for indication of the operative mode thereof.

7. The structure set forth in claim 1 and switching means connected to said probes and said first and second timing means, said switching means arranged to activate and deactivate said first timing means in response to conduction between said first and third probes and activating said second timing means upon deactivation of said first timing means.

8. The structure set forth in claim 7 and said switching means deactivating said second timing means when conduction between said first and second probes is interrupted.

9. The structure set forth in claim 1 and said supporting means including a longitudinally extending housing member surrounding said probes.

10. The structure set forth in claim 9 and said probes being spaced within said housing.

11. The structure set forth in claim 9 and said housing being of a non-electrically conductive material.

12. The structure set forth in claim 10 and said first probe being arranged to extend from one lower end of said housing to the upper end thereof.

13. The structure set forth in claim 9 and one of said second or third probes being vertically adjustable within said housing.

* * * * *